United States Patent
Wesselmann et al.

(10) Patent No.: US 8,512,369 B2
(45) Date of Patent: Aug. 20, 2013

(54) COMBINED ROLLING MEMBRANE-BALLOON CATHETER

(75) Inventors: Matthias Wesselmann, Ruedlingen (CH); Hans Lang, Buchs (CH); Susanne Pfenninger-Ganz, Aathal (CH)

(73) Assignee: Biotronik AG, Buelach (CH)

( * ) Notice: Subject to any disclaimer, the term of this patent is extended or adjusted under 35 U.S.C. 154(b) by 257 days.

(21) Appl. No.: 13/090,520

(22) Filed: Apr. 20, 2011

(65) Prior Publication Data

US 2011/0270296 A1 Nov. 3, 2011

Related U.S. Application Data

(60) Provisional application No. 61/328,650, filed on Apr. 28, 2010.

(51) Int. Cl.
  *A61M 29/00* (2006.01)
(52) U.S. Cl.
  USPC .......................................................... 606/192
(58) Field of Classification Search
  USPC ................. 604/264, 271, 523, 524, 525, 526, 604/527, 528; 606/191, 192, 193, 194, 195, 606/196, 197, 198, 199
  See application file for complete search history.

(56) References Cited

U.S. PATENT DOCUMENTS

| | | | | |
|---|---|---|---|---|
| 4,243,040 A | * | 1/1981 | Beecher | 606/127 |
| 4,271,839 A | * | 6/1981 | Fogarty et al. | 606/194 |
| 4,479,497 A | * | 10/1984 | Fogarty et al. | 606/194 |
| 4,493,711 A | * | 1/1985 | Chin et al. | 604/271 |
| 5,074,845 A | * | 12/1991 | Miraki et al. | 604/103.08 |
| 5,364,345 A | | 11/1994 | Lowery et al. | |
| 5,447,497 A | * | 9/1995 | Sogard et al. | 604/101.02 |
| 5,593,418 A | * | 1/1997 | Mollenauer | 606/192 |
| 5,735,859 A | * | 4/1998 | Fischell et al. | 606/108 |
| 6,989,009 B2 | * | 1/2006 | Lafontaine | 606/20 |
| 7,220,252 B2 | * | 5/2007 | Shah | 604/500 |
| 2009/0254063 A1 | | 10/2009 | Von Oepen et al. | |

OTHER PUBLICATIONS

German Search Report for Parent Application No. EP 11 16 1562.

* cited by examiner

*Primary Examiner* — Ryan Severson
*Assistant Examiner* — Jonathan W Miles
(74) *Attorney, Agent, or Firm* — Biotech Beach Law Group PC

(57) ABSTRACT

A combined rolling membrane-balloon catheter, in particular for expanding stenoses in bodily vessels, including: an outer shaft (1) and an inner shaft (4) which is axially displaceable therein, an intermediate shaft (7) situated between the inner and outer shafts (4, 1) which is likewise axially displaceable, a rolling membrane (12) which is attached in a pressure-tight manner between the distal end (2) of the outer shaft (1) and the distal end (11) of the inner shaft (4), and which may be displaced between a passive position within the outer shaft (1) and an active position which is distally expanded from the outer shaft (1) by the action of pressure, and a dilatable balloon (14) which is attached in a pressure-tight manner between the distal end (11) of the inner shaft (4) and the distal end of the intermediate shaft (7), and which may be displaced between a passive position within the outer shaft (1) and proximally in front of the rolling membrane (12), and an active position which is distally expanded from the outer shaft (1), within the rolling membrane (12), by the action of pressure.

13 Claims, 8 Drawing Sheets

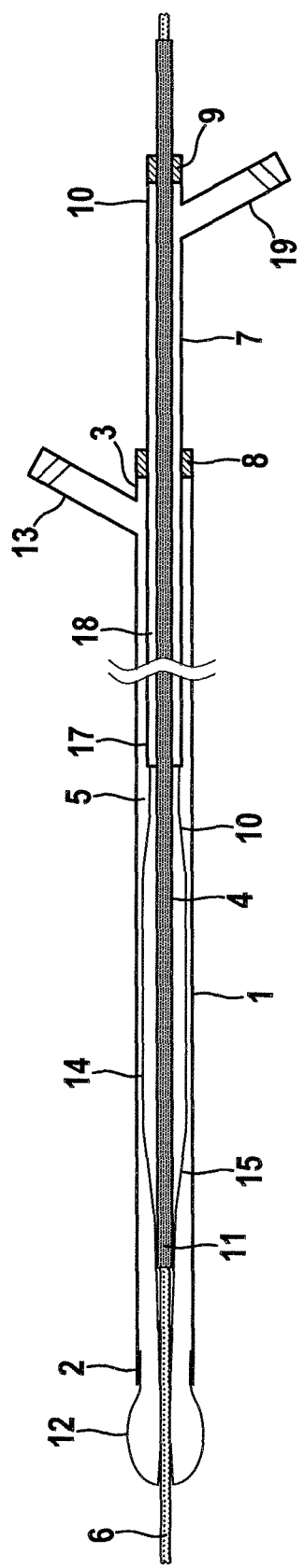

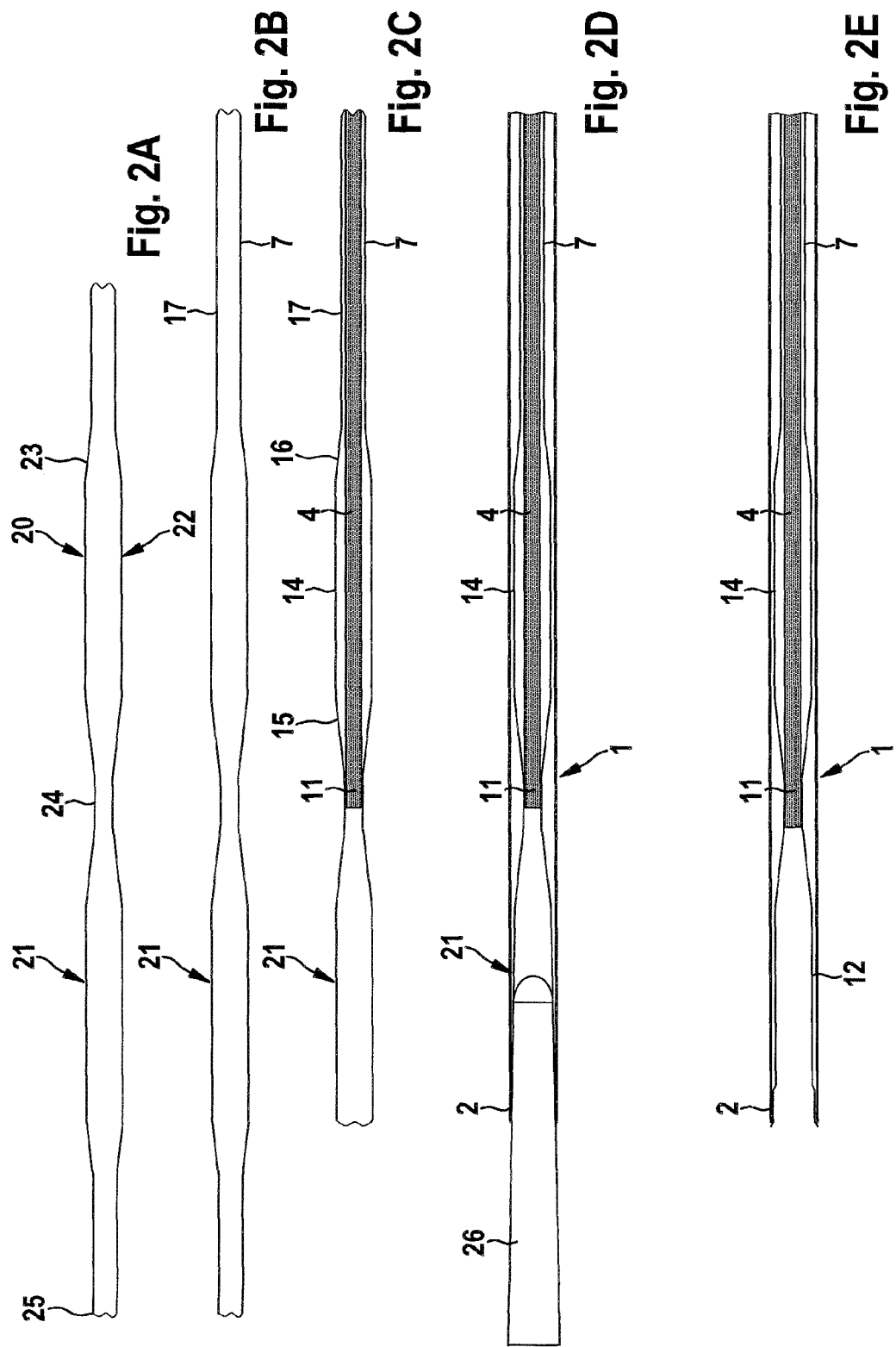

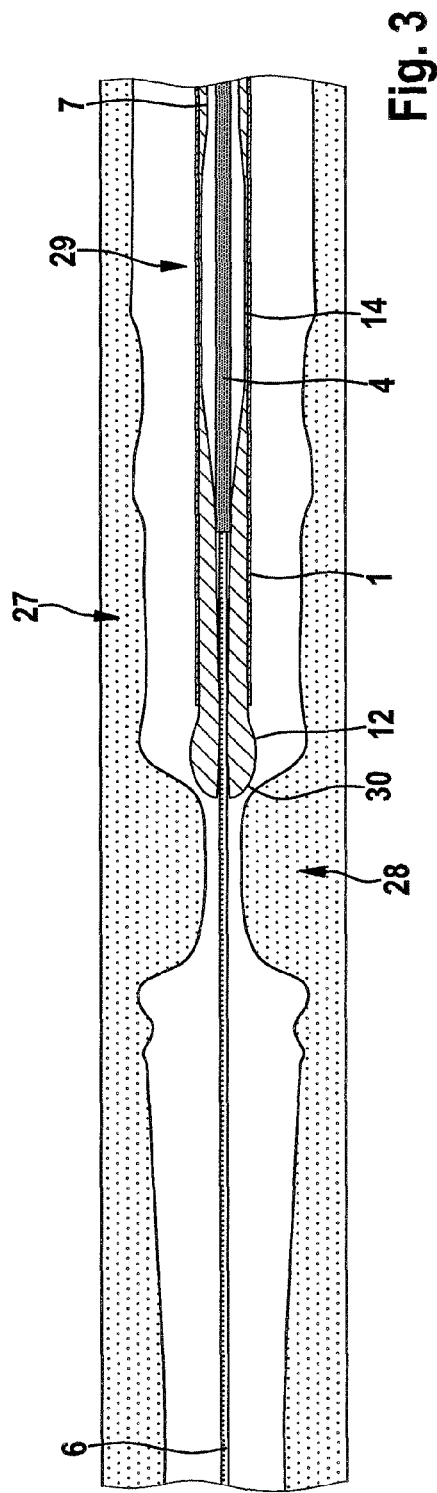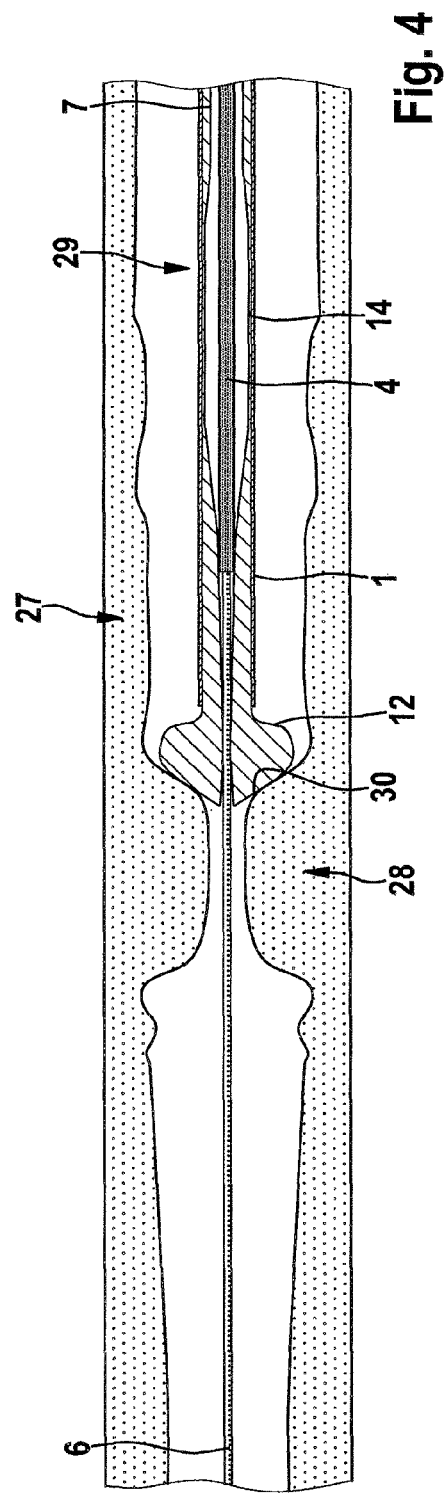

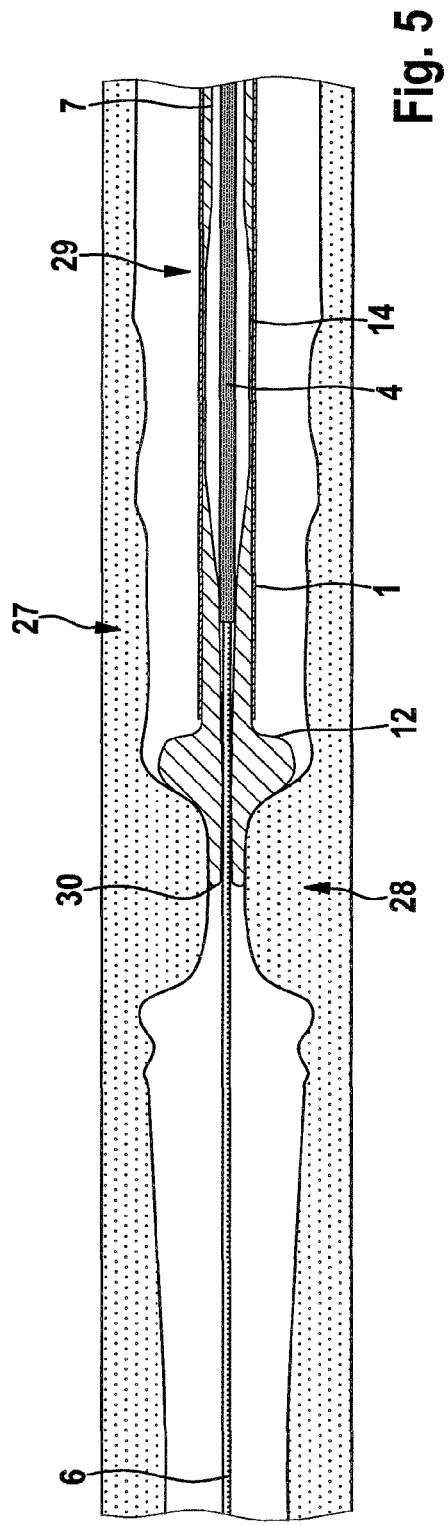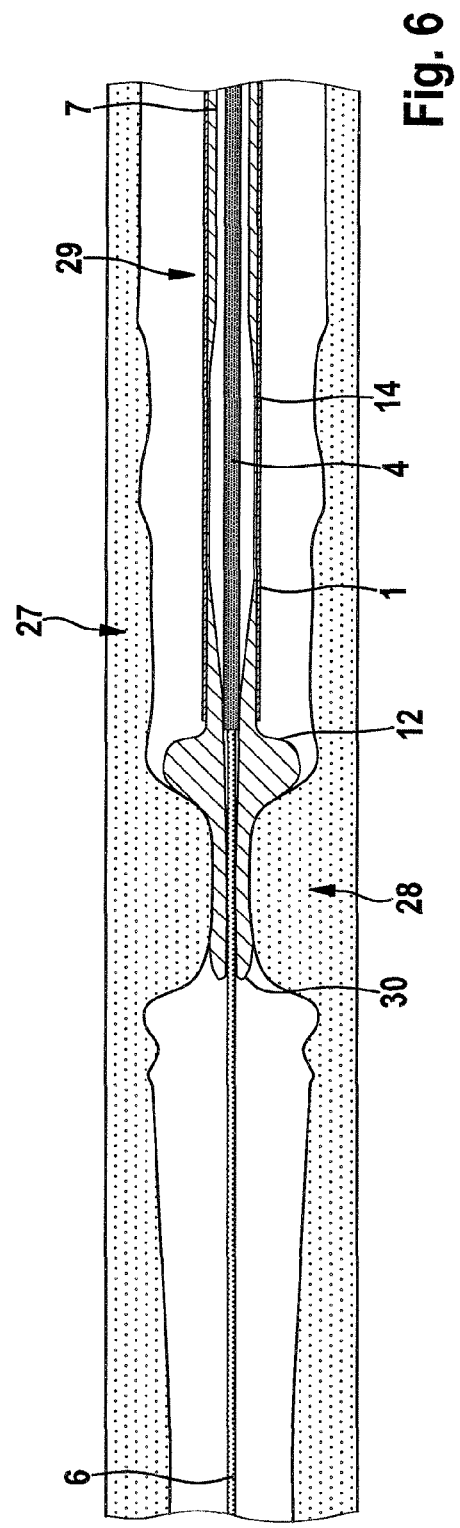

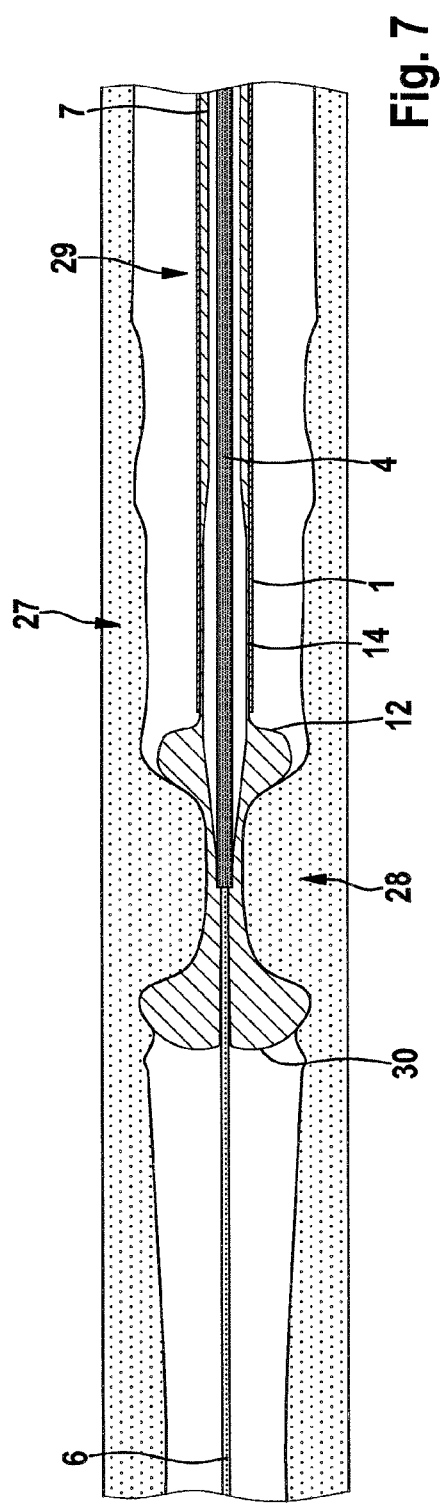

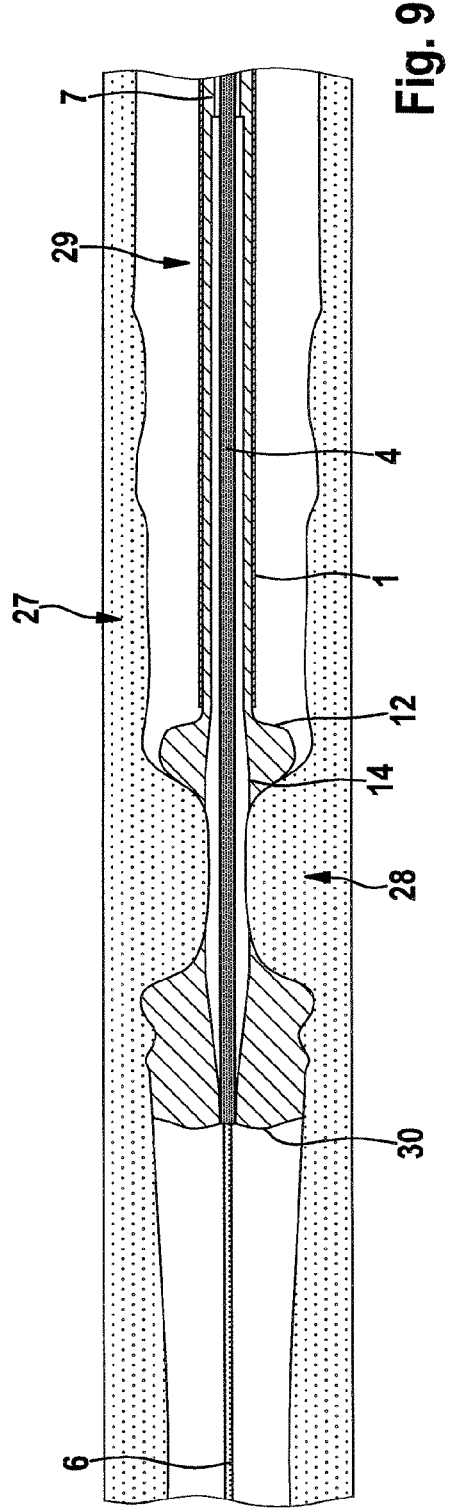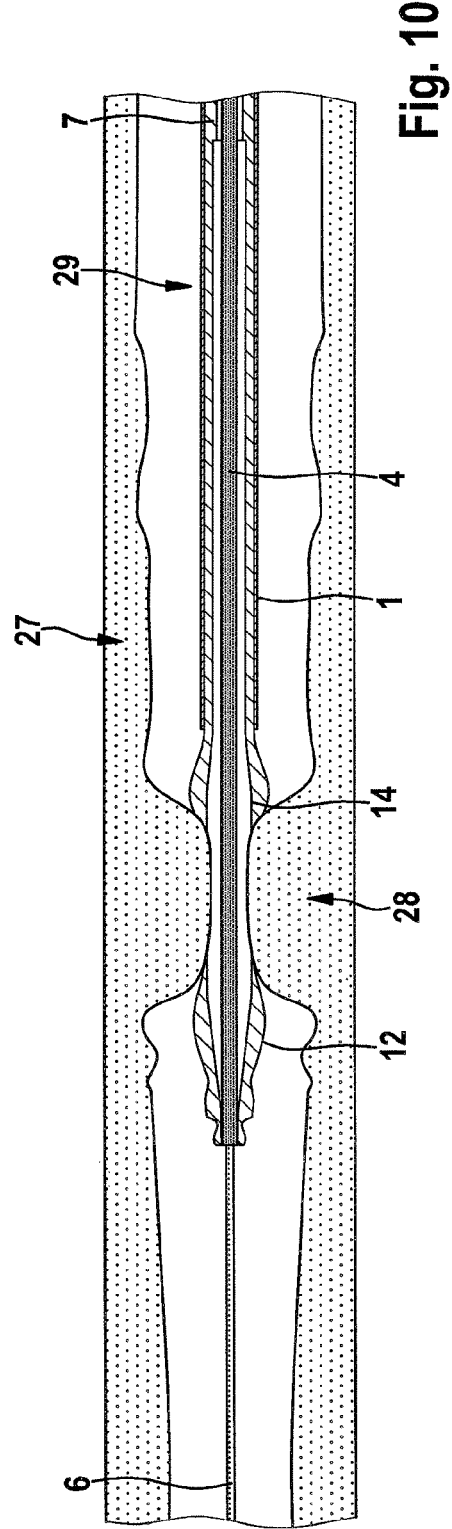

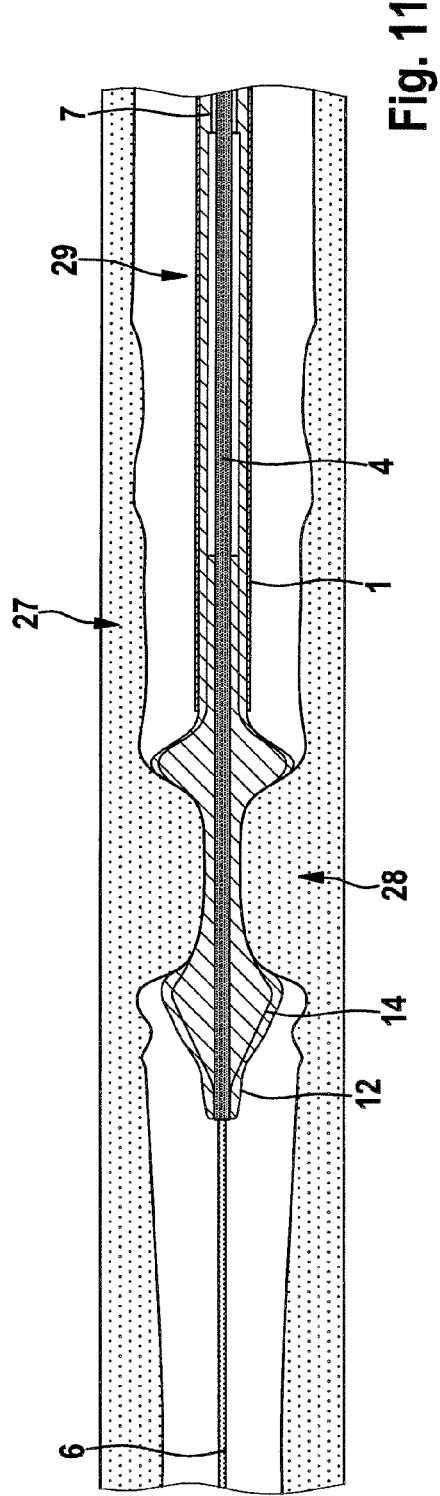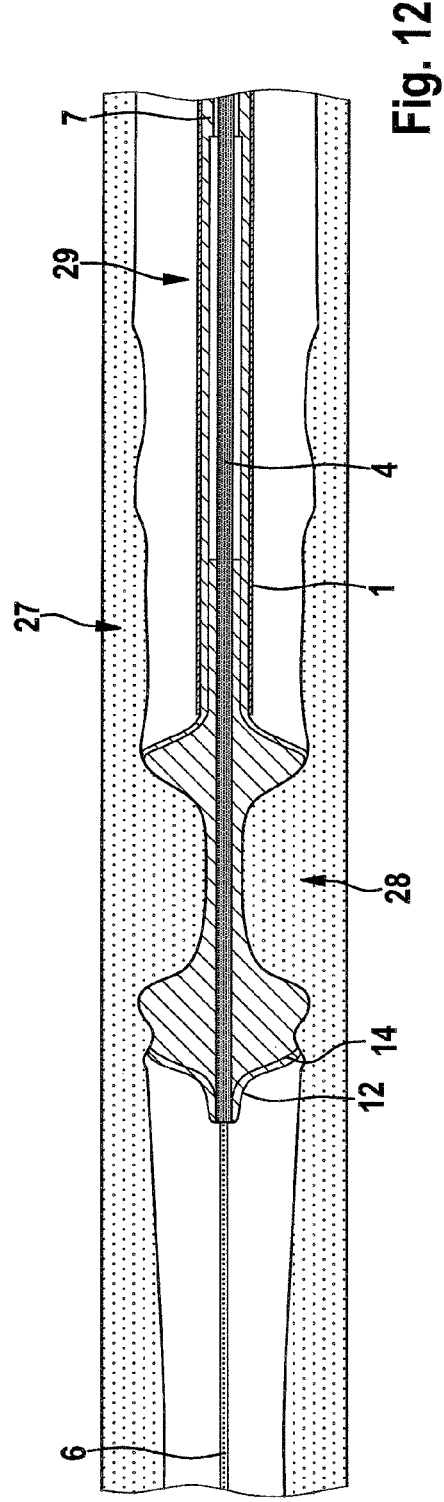

COMBINED ROLLING MEMBRANE-BALLOON CATHETER

CROSS REFERENCE TO RELATED APPLICATIONS

This invention claims benefit of priority to U.S. patent application Ser. No. 61/328,650, filed on Apr. 28, 2010; the contents of which are herein incorporated by reference in their entirety.

TECHNICAL FIELD

The invention relates to a combined rolling membrane-balloon catheter, in particular for expanding stenoses in bodily vessels, having an outer shaft and an inner shaft which is axially displaceable therein.

BACKGROUND

A combined rolling membrane-balloon catheter is known from U.S. Pat. No. 5,662,703 A which is designed for deploying a self-expanding stent in the region of a stenosis in a bodily vessel. This catheter has an inner and an outer shaft, between the distal ends of which a rolling membrane which is doubled over on itself is provided, and which forms the distal end of the catheter. This rolling membrane forms a space, extending coaxially with the catheter, in front of the distal end of the inner shaft in which the self-expanding stent is accommodated in its contracted state.

A balloon which is expandable when acted on by pressure is proximally situated in front of the distal end of the inner shaft, and is used to assist in the expansion motion of the stent.

To be released, the outer shaft is moved relative to the inner shaft in the proximal direction, as a result of which the membrane which is doubled over on itself is retracted from the stent in a peeling motion to the rear, and gradually releases the stent. The stent gradually widens due to its self-expansion action until it is released as a result of the complete peeling of the rolling membrane to the rear. At the same time, the rolling membrane is pulled over the balloon in the proximal direction, the balloon then being, situated directly in front of the distal end of the catheter. The catheter may then be inserted into the expanded stent in the axial direction, and the balloon may be expanded by the action of pressure. The stent is thus optimally expanded, and stenoses present in the bodily vessel are also mechanically expanded. Since the balloon is present inside the rolling membrane, the entire system is particularly pressure-tight. If the balloon bursts, the rolling membrane situated around the balloon prevents the highly pressurized fluid from escaping into the bodily vessel. Instead, the pressure is relieved via the interior of the outer catheter.

A device for removing vein sections is known from U.S. Pat. No. 5,593,418 A, in which a rolling membrane is provided which may be unrolled over the vein to be removed, using a pressurized fluid. This device also has an anchoring balloon which is inflated inside the vein before the rolling membrane is unrolled in order to fix the vein with respect to the rolling membrane.

As background for the invention, it is further noted that basic requirements are imposed on the catheter used in the treatment of stenoses in bodily vessels. Thus, penetration into even narrow lesions with major damage should be possible with minimum friction, and at the same time, for achieving high expansion forces it should be possible for the balloons used to be acted on with high pressure. The balloons must have a correspondingly high pressure resistance, so that they are generally more rigid with regard to their material characteristics. In turn, this causes problems for penetration into narrow, damaged bodily vessels.

In the present interplay of various conflicting problems, rolling membrane catheters are basically known which, although they are able to penetrate into a stenosis or severely damaged vessel regions with very little friction, due to the necessity of rolling them over, such rolling membranes are very difficult to connect to a balloon lumen in a pressure-tight manner.

In addition, hydrophilic coatings of conventional balloon catheters are known for which, although the coefficient of friction for the balloon catheter may be greatly reduced, such a catheter may still become stuck in long, severely damaged lesions. Thus, as a rule a compromise must be found between flexibility and pushability of the catheter, which possibly may not be optimal for all clinical cases.

Lastly, another fundamental problem with such balloon catheters is that they are generally not anchored at their treatment site, i.e., in the region of a stenosis, for example.

SUMMARY

Based on the described problems of the prior art, the object of the present invention is to refine a combined rolling membrane-balloon catheter in such a way that it may be easily introduced into problematic bodily vessel zones, with low bending resistance and with the greatest possible exclusion of friction, while reliably producing a high dilation force at that location with anchoring in front of a stenosis.

This object is achieved by providing a combined rolling membrane-balloon catheter capable of expanding stenoses in bodily vessels. The catheter includes an outer shaft and an inner shaft which is axially displaceable therein. The catheter also includes an intermediate shaft situated between the inner and outer shafts which is likewise axially displaceable; a rolling membrane which is attached in a pressure-tight manner between the distal end of the outer shaft and the distal end of the inner shaft, and which may be displaced between a passive position within the outer shaft and an active position which is distally expanded from the outer shaft by the action of pressure, and a dilatable balloon which is attached in a pressure-tight manner between the distal end of the inner shaft and the distal end of the intermediate shaft, and which may be displaced between a passive position within the outer shaft and proximally in front of the rolling membrane, and an active position which is distally expanded from the outer shaft, within the rolling membrane, by the action of pressure.

In some embodiments the inner shaft includes a lumen for a guide wire to position the catheter. During expansion of the rolling membrane from the outer shaft, the inner shaft, while carrying along the balloon together with the intermediate shaft, can be progressively inserted into the rolling membrane which is unrolling in the expansion.

In some embodiments for pressure impingement on the rolling membrane, an annular space between the intermediate shaft and the outer shaft is provided with a pressurized fluid line which is proximally connected to a membrane pressure joint on the outer shaft. In other embodiments, the annular space between the intermediate shaft and the inner shaft is provided as a pressurized fluid line which is proximally connected to a balloon pressure joint on the intermediate shaft.

In some embodiments, the intermediate shaft is guided in an axially displaceable manner in a pressure-tight ring seal at the proximal end of the outer shaft.

In some embodiments the rolling membrane and the balloon are both provided as a single tubular section. When transitioning from its passive to its active position, the rolling membrane may be expanded in an unrolling motion, distally superimposed with a radial expansion motion. Further, the rolling membrane may be deflated before the balloon is expanded.

The skilled artisan will appreciate the catheter represents a synthesis of a rolling membrane and a conventional balloon catheter which has the following advantages: First, friction is minimized as a result of the unrolling of the exterior rolling membrane and the liquid friction between the membrane and the balloon due to the pressurized fluid used for the pressure impingement. Second, the catheter is anchored in front of the stenosis as the result of inflating the rolling membrane which is expanding into the active position. Third, the wall emerging in the distal direction during the transition between the passive and active positions of the rolling membrane produces a thrust force which is proportional to the cross section of this distal wall and to the hydraulic pressure. The pressure force is thus delivered without loss to the application site in the region of the stenosis.

Fourth, the bending resistance of the combined rolling membrane-balloon catheter is reduced due to the fact that when the catheter is inserted at the region of a stenosis, the rolling membrane and the balloon are situated one behind the other within the catheter outer shaft, i.e., project only minimally in the radial direction. To pass through the stenosis it is necessary to bend only the balloon.

Fifth, since the rolling membrane and the balloon situated therein in the active position together form a so-called double-membrane balloon, this formation is able to withstand much higher pressures. The balloon wall may therefore have an overall thinner design, which in turn reduces the bending resistance of the system. In addition, the taper of the balloon is more flexible due to the reduced wall thickness.

Sixth, the described method for producing a double balloon catheter is particularly advantageous for manufacture in comparison to known double balloon catheter structures. In the latter case, two balloons are formed in succession, and the inner balloon is then inserted into the narrow neck of the outer balloon.

Seventh, the configuration of the balloon itself corresponds to known designs which have proven to be effective, and whose pressure-tightness is thus ensured. The exterior rolling membrane also supports the interior balloon.

In a second aspect of the invention a method for manufacturing such a combined rolling membrane-balloon catheter is provided, characterized by the following method steps:

Producing two balloon blanks, axially positioned one behind the other, from a section of tubing, Attaching the proximal end of the proximal balloon blank to the distal end of the catheter intermediate shaft, Attaching the distal end of the proximal balloon blank to the distal end of the inner shaft, Inserting the assembly composed of the balloon blanks and the inner shaft and intermediate shaft into the outer shaft, and Attaching the distal end of the distal balloon blank, which functions as a rolling membrane, to the distal end of the outer shaft.

Alternatively, the two balloon blanks may be produced by thermoforming from a single section of tubing, or may also be formed separately. The two balloon blanks may then be attached to the inner, intermediate, and/or outer shaft of the catheter by welding or gluing.

DESCRIPTION OF THE DRAWINGS

Features, particulars, and advantages in this regard result from the following description of an exemplary embodiment with reference to the accompanying drawings, which show the following:

FIG. 1 shows a schematic axial section of a rolling membrane-balloon catheter;

FIGS. 2A-2E show schematic illustrations of the manufacture of the catheter according to FIG. 1 in successive production steps; and FIGS. 3-13 show schematic longitudinal sections of a bodily vessel in the region of a stenosis, together with a rolling membrane-balloon catheter in successive treatment steps.

DETAILED DESCRIPTION

Figure 13:
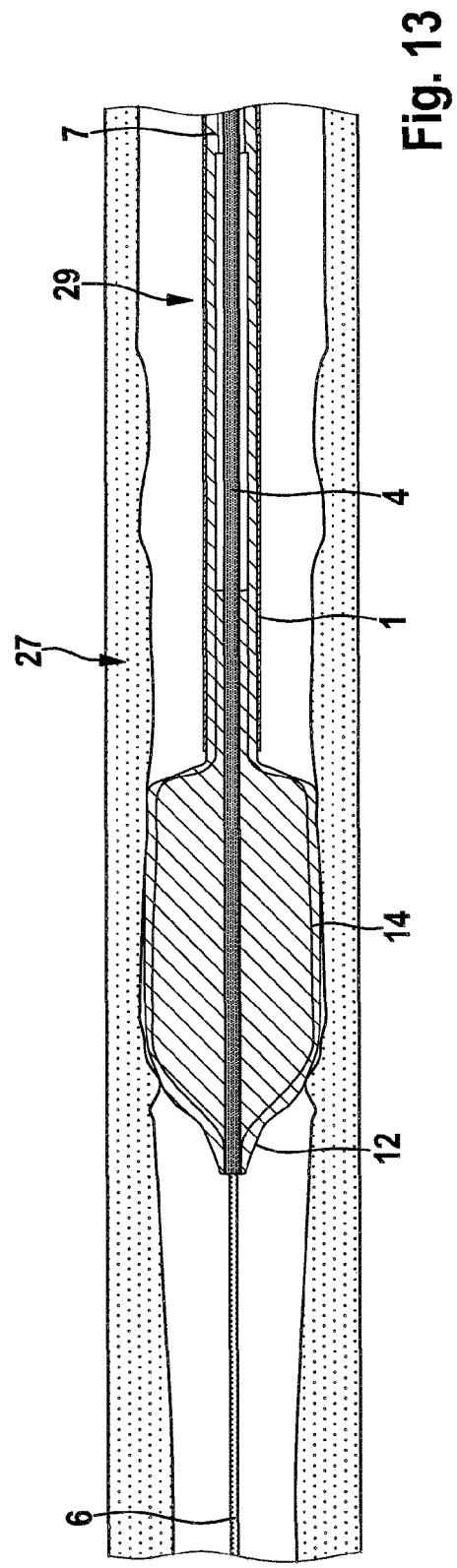

As shown in FIG. 1, the illustrated rolling membrane-balloon catheter has an elongated outer shaft 1 having a distal end 2 with which it may be inserted into a bodily vessel, and a proximal end 3. An inner shaft 4 situated in the outer shaft 1 has a much smaller diameter than the outer shaft, and accordingly together with the outer shaft 1 forms an annular space 5. Situated in the inner shaft 4 is a lumen (not illustrated), by means of which the catheter may be pushed via a guide wire 6 to the treatment site in a bodily vessel.

In addition, an intermediate shaft 7 is situated between the outer shaft 1 and the inner shaft 4, coaxial with the two shafts 1, 4, and together with the inner shaft 4 may be axially displaced with respect to the outer shaft 1. For this purpose, the intermediate shaft 7 is displaceable in a ring seal 8 in the form of a so-called Tuohy Borst seal, for example, which proximally closes off the annular space 5 in a pressure-tight manner. The inner shaft 4, in turn, is guided in a pressure-tight manner through an end plug 9 at the proximal end 10.

A rolling membrane 12 is situated between the distal end 2 of the outer shaft 1 and the distal end 11 of the inner shaft 4, and in FIG. 1 is illustrated in a position that is already slightly pushed out from the outer shaft 1. The actual passive position of the rolling membrane 12 within the outer shaft 1 is identifiable in FIG. 2E, The rolling membrane 12 is connected in a pressure-tight manner to the outer shaft 1 and the inner shaft 2 (sic; 4) by means of appropriate welds, and via the annular space 5 may be acted on by a pressurized fluid which may be introduced under pressure through the membrane pressure joint 13 at the proximal end 3 of the outer shaft 1.

In addition, a balloon 14 is proximally situated within the outer shaft 1, in front of the rolling membrane 12, and the distal taper 15 of the balloon is attached to the distal end 11 of the inner shaft 4 in a pressure-tight manner. The proximal taper of the balloon 14 in turn is mounted on the distal end 17 of the intermediate shaft 7 in a pressure-tight manner. Via the annular space 18 which is formed between the inner shaft 4 and the intermediate shaft 7, the balloon 14 may be acted on by a pressurized fluid which may be introduced through a balloon pressure joint 19 at the proximal end 10 of the intermediate shaft 7.

The manufacture of the combined rolling membrane-balloon catheter according to FIG. 1 may be explained in greater detail with reference to FIGS. 2A through 2E. Starting with a single continuous section of tubing 20, two balloon blanks 21, 22 axially positioned one behind the other are produced by thermoforming, the first balloon blank 21 subsequently forming the rolling membrane 12, and the second balloon blank 22 subsequently forming the actual balloon 14 (FIG. 2A). The proximal end 23 of the proximal balloon blank 22 is attached to the distal end 17 of the intermediate shaft 7 by welding, for example (FIG. 2B).

In the transition region between the two balloon blanks 21, 22 the section of tubing 20 is then attached to the distal end 11 of the inner shaft 4, once again by welding, for example, so that the distal end 24 of the proximal balloon blank 22 is fixed in place at that location. The balloon 14 of the catheter is thus defined based on the balloon blank 22 (see FIG. 2C).

In the next production step the entire assembly composed of the balloon blanks 21, 22, the inner shaft 4, and the intermediate shaft 7 is inserted into the outer shaft 1, and the distal end 25 of the distal balloon blank 21 is attached to the distal end 2 of the outer shaft 7 (sic; 1) by welding or gluing with the aid of a tool 26 inserted into the outer shaft 1 (FIG. 2D).

This results in the finished rolling membrane-balloon catheter, as illustrated in FIG. 2E in the passive position of the balloon 14 and the rolling membrane 12 within the outer shaft 1.

The clinical use of the combined rolling membrane-balloon catheter 29 is explained with reference to FIGS. 3 through 13. These figures show a bodily vessel 27 with a pathological constriction in the form of a stenosis 28. The catheter 29 is pushed onto the guide wire 6, which has previously been guided through the stenosis 28, until reaching the stenosis 28 (FIG. 3). In this passive position of the rolling membrane 12 a pressurized fluid is introduced via the membrane pressure joint 13 into the annular space 5 between the inner and outer shafts 4, 1, respectively, the pressurized fluid flowing past the folded balloon 14 and causing the rolling membrane 12 to inflate. By moving the inner shaft 4 and intermediate shaft 7 together in the distal direction, during this inflation the rolling membrane 12 is able to distally emerge from the front of the outer shaft 1 on the guide wire 6 into its active position, and to expand in the radial direction (FIG. 4). The catheter 29 is thus anchored in front of the stenosis 28. Upon further pressure impingement the advancing wall of the rolling membrane 12 penetrates into the region between the guide wire 6 and the stenosis 28, since the hydraulic pressure on this distal wall 30 provides a localized thrust force. This thrust force draws the inner shaft 4 in further (FIG. 5) until the rolling membrane 12 has passed through the stenosis 28 (FIG. 6) and likewise expands in the radial direction behind the stenosis (FIG. 7). The inner shaft 4 together with the intermediate shaft 7 and the balloon 14 is progressively drawn from the outer shaft 1, and is likewise gradually drawn into the region of the stenosis 28. As clearly shown in FIGS. 8 and 9, this motion continues until the balloon 14 as well, starting from its passive position within the outer shaft 1, is completely centrally placed in the stenosis 28 in the active position, shown in FIG. 9, outside the outer shaft 1. In this position the action of pressure on the rolling membrane 12 is relieved, so that radially external pressure also no longer acts on the balloon 14 (FIG. 10). The requirement is thus met that the balloon 14 may be acted on by pressure by introducing a pressurized fluid through the balloon pressure joint 19. The balloon dilates over its entire length, thus completely expanding the stenosis 28 in the radial direction, as clearly shown in FIGS. 11 through 13.

After the balloon 14 is relieved of pressure, the entire catheter 29 may be withdrawn from the bodily vessel 27.

Based on the preceding description of the medical use of the catheter, various advantages once again become clear. For example, in the catheter according to the invention, the static and sliding friction in typical rolling membrane designs is replaced by rolling friction within the rolling membrane 12. Second, as shown in FIGS. 5 through 8, the catheter together with its rolling membrane 12 may be wedged into even narrow gaps without appreciable friction. Third, improved capability for advancing, i.e., high "pushability," at the treatment site may be achieved due to the hydraulic propulsion of the rolling membrane. The system generates its thrust force at the location where it is needed; there are no friction losses along the shaft itself. Fourth, the rolling membrane may be anchored in front of the stenosis, thus further improving the ability of the treatment device to penetrate into the stenosis. Fifth, the catheter may be pushed more easily along the guide wire during insertion due to the arrangement of the rolling membrane 12 and the balloon 14 one behind the other. Sixth, the catheter is less sensitive to leakage effects such as so-called pin holes. Seventh, the clinical use of the device is comparatively simple and logically broken down with regard to the sequence of the individual steps.

It will be apparent to those skilled in the art that numerous modifications and variations of the described examples and embodiments are possible in light of the above teaching. The disclosed examples and embodiments are presented for purposes of illustration only. Other alternate embodiments may include some or all of the features disclosed herein. Therefore, it is the intent to cover all such modifications and alternate embodiments as may come within the true scope of this invention.

What is claimed is:

1. A combined rolling membrane-balloon catheter capable of expanding stenoses in bodily vessels, comprising:
    an outer shaft; and
    an inner shaft which is axially displaceable therein; characterized by
    an intermediate shaft situated between the inner and outer shafts which is likewise axially displaceable;
    a rolling membrane which is attached in a pressure-tight manner between a distal end of the outer shaft and a distal end of the inner shaft, and which may be displaced between a passive position within the outer shaft and an active position which is distally expanded from the outer shaft by the action of pressure; and
    a dilatable balloon which is attached in a pressure-tight manner between the distal end of the inner shaft and a distal end of the intermediate shaft, and which may be displaced between a passive position within the outer shaft and proximally in front of the rolling membrane, and an active position which is distally expanded from the outer shaft, within the rolling membrane, by the action of pressure.

2. Rolling membrane-balloon catheter according to claim 1, characterized in that the inner shaft comprises a lumen for a guide wire for positioning the catheter.

3. Rolling membrane-balloon catheter according to claim 1, characterized in that during expansion of the rolling membrane from the outer shaft, the inner shaft, while carrying along the balloon together with the intermediate shaft, is progressively inserted into the rolling membrane which is unrolling during the expansion.

4. Rolling membrane-balloon catheter according to claim 1, characterized in that for pressure impingement on the rolling membrane, an annular space between the intermediate shaft and the outer shaft is provided with a pressurized fluid line which is proximally connected to a membrane pressure joint on the outer shaft.

5. Rolling membrane-balloon catheter according to claim 1, characterized in that for the pressure impingement on the balloon, the annular space between the intermediate shaft and the inner shaft is provided as a pressurized fluid line which is proximally connected to a balloon pressure joint on the intermediate shaft.

6. Rolling membrane-balloon catheter according to claim 1, characterized in that the intermediate shaft is guided in an axially displaceable manner in a pressure-tight ring seal at a proximal end of the outer shaft.

7. Rolling membrane-balloon catheter according to claim 1, characterized in that the rolling membrane and the balloon are both composed of a single tubular section.

8. Rolling membrane-balloon catheter according to claim 1, characterized in that during transition from its passive to its active position, the rolling membrane may be expanded in an unrolling motion, distally superimposed with a radial expansion motion.

9. Rolling membrane-balloon catheter according to claim 1, characterized in that the rolling membrane may be deflated before the balloon is expanded.

10. Method for manufacturing the combined rolling membrane-balloon catheter according to claim 1, characterized by the following method steps:

producing two balloon blanks, which are axially positioned one behind the other, from a section of tubing;

attaching a proximal end of a proximal balloon blank to the distal end of the catheter intermediate shaft;

attaching a distal end of a proximal balloon blank to the distal end of the inner shaft;

inserting an assembly composed of the balloon blanks and the inner shaft and intermediate shaft into the outer shaft; and attaching a distal end of a distal balloon blank, which functions as a rolling membrane, to the distal end of the outer shaft.

11. Method according to claim 10, characterized in that the two balloon blanks are produced by thermoforming from a single section of tubing.

12. Method according to claim 10, characterized in that the two balloon blanks are formed separately.

13. Method according to claim 10, characterized in that the two balloon blanks are attached to the inner, intermediate, and/or outer shaft by welding or gluing.

* * * * *